(12) United States Patent
Moffitt et al.

(10) Patent No.: US 7,877,136 B1
(45) Date of Patent: Jan. 25, 2011

(54) ENHANCEMENT OF NEURAL SIGNAL TRANSMISSION THROUGH DAMAGED NEURAL TISSUE VIA HYPERPOLARIZING ELECTRICAL STIMULATION CURRENT

(75) Inventors: Michael A. Moffitt, Valencia, CA (US); Kristen N. Jaax, Santa Clarita, CA (US); Rafael Carbunaru, Valley Village, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 634 days.

(21) Appl. No.: 11/864,494

(22) Filed: Sep. 28, 2007

(51) Int. Cl.
*A61N 1/36* (2006.01)
(52) U.S. Cl. .............................. 607/2; 607/48
(58) Field of Classification Search ................ 607/2, 607/46, 48, 50
See application file for complete search history.

(56) References Cited

U.S. PATENT DOCUMENTS

| | | |
|---|---|---|
| 3,850,161 A | 11/1974 | Liss |
| 3,881,495 A | 5/1975 | Pannozzo et al. |
| 3,941,136 A | 3/1976 | Bucalo |
| 4,408,608 A | 10/1983 | Daly et al. |
| 4,467,809 A | 8/1984 | Brighton |
| 4,542,753 A | 9/1985 | Brenman et al. |
| 4,585,005 A | 4/1986 | Lue et al. |
| 4,590,946 A | 5/1986 | Loeb |
| 4,602,624 A | 7/1986 | Naples et al. |
| 4,608,985 A | 9/1986 | Crish et al. |
| 4,628,942 A | 12/1986 | Sweeney et al. |
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,993,413 A | 2/1991 | McLeod et al. |
| 5,095,904 A | 3/1992 | Seligman |
| 5,188,104 A | 2/1993 | Wernicke et al. |
| 5,193,539 A | 3/1993 | Schulman et al. |
| 5,193,540 A | 3/1993 | Schulman et al. |
| 5,199,430 A | 4/1993 | Fang et al. |
| 5,211,129 A | 5/1993 | Taylor et al. |
| 5,215,086 A | 6/1993 | Terry et al. |
| 5,299,569 A | 4/1994 | Wernicke et al. |

(Continued)

FOREIGN PATENT DOCUMENTS

WO    WO-98/37926 A1    9/1998

(Continued)

OTHER PUBLICATIONS

U.S. Appl. No. 60/383,157, filed May 23, 2002.

(Continued)

*Primary Examiner*—Carl H Layno
*Assistant Examiner*—Brian T Gedeon
(74) *Attorney, Agent, or Firm*—Frommer Lawrence & Haug LLP; Bruce E. Black

(57) ABSTRACT

Methods and systems of enhancing transmission of a neural signal through damaged neural tissue include providing a stimulator, programming the stimulator with one or more stimulation parameters configured to enhance transmission of a neural signal through the damaged neural tissue, and applying a hyperpolarizing electrical stimulation current with the stimulator to the damaged neural tissue in accordance with the one or more stimulation parameters.

18 Claims, 15 Drawing Sheets

U.S. PATENT DOCUMENTS

| | | |
|---|---|---|
| 5,312,439 A | 5/1994 | Loeb |
| 5,314,451 A | 5/1994 | Mulier |
| 5,314,458 A | 5/1994 | Najafi et al. |
| 5,324,316 A | 6/1994 | Schulman et al. |
| 5,330,515 A | 7/1994 | Rutecki et al. |
| 5,358,514 A | 10/1994 | Schulman et al. |
| 5,400,784 A | 3/1995 | Durand et al. |
| 5,405,363 A | 4/1995 | Kroll et al. |
| 5,405,367 A | 4/1995 | Schulman et al. |
| 5,439,938 A | 8/1995 | Snyder et al. |
| 5,454,840 A | 10/1995 | Krakovsky et al. |
| 5,505,201 A | 4/1996 | Grill, Jr. et al. |
| 5,513,636 A | 5/1996 | Palti |
| 5,515,848 A | 5/1996 | Corbett, III et al. |
| 5,531,778 A | 7/1996 | Maschino et al. |
| 5,531,787 A | 7/1996 | Lesinski et al. |
| 5,571,118 A | 11/1996 | Boutos |
| 5,571,148 A | 11/1996 | Loeb et al. |
| 5,634,462 A | 6/1997 | Tyler et al. |
| 5,649,970 A | 7/1997 | Loeb et al. |
| 5,700,282 A | 12/1997 | Zabara |
| 5,713,922 A | 2/1998 | King |
| 5,752,979 A | 5/1998 | Benabid |
| 5,755,750 A | 5/1998 | Petruska et al. |
| 5,775,331 A | 7/1998 | Raymond et al. |
| 5,782,891 A | 7/1998 | Hassler et al. |
| 5,895,416 A | 4/1999 | Barreras, Sr. et al. |
| 5,899,933 A | 5/1999 | Bhadra et al. |
| 5,938,584 A | 8/1999 | Ardito et al. |
| 5,995,868 A | 11/1999 | Dorfmeister et al. |
| 6,051,017 A | 4/2000 | Loeb et al. |
| 6,058,331 A | 5/2000 | King |
| 6,104,956 A | 8/2000 | Naritoku et al. |
| 6,136,019 A * | 10/2000 | Mower ........................ 607/9 |
| 6,154,678 A | 11/2000 | Lauro |
| 6,178,349 B1 | 1/2001 | Kieval |
| 6,198,970 B1 | 3/2001 | Freed et al. |
| 6,205,359 B1 | 3/2001 | Boveja |
| 6,214,032 B1 | 4/2001 | Loeb et al. |
| 6,216,045 B1 | 4/2001 | Black et al. |
| 6,226,552 B1 | 5/2001 | Staunton et al. |
| 6,275,737 B1 | 8/2001 | Mann |
| 6,341,236 B1 | 1/2002 | Osorio et al. |
| 6,424,234 B1 | 7/2002 | Stevenson |
| 6,473,652 B1 | 10/2002 | Sarwal et al. |
| 6,505,078 B1 | 1/2003 | King et al. |
| 6,560,490 B2 | 5/2003 | Grill et al. |
| 6,597,954 B1 | 7/2003 | Pless et al. |
| 6,600,954 B2 | 7/2003 | Cohen et al. |
| 6,622,048 B1 | 9/2003 | Mann et al. |
| 6,650,943 B1 | 11/2003 | Whitehurst et al. |
| 6,662,035 B2 | 12/2003 | Sochor |
| 6,665,562 B2 | 12/2003 | Gluckman et al. |
| 6,675,046 B2 * | 1/2004 | Holsheimer ................ 607/46 |
| 6,684,105 B2 | 1/2004 | Cohen et al. |
| 6,712,753 B2 | 3/2004 | Manne |
| 6,782,292 B2 | 8/2004 | Whitehurst |
| 6,826,428 B1 | 11/2004 | Chen et al. |
| 6,892,097 B2 | 5/2005 | Holsheimer |
| 6,928,320 B2 | 8/2005 | King |
| 7,054,692 B1 | 5/2006 | Whitehurst et al. |
| 7,072,720 B2 | 7/2006 | Puskas |
| 7,203,548 B2 | 4/2007 | Whitehurst et al. |
| 7,292,890 B2 | 11/2007 | Whitehurst et al. |
| 2001/0003799 A1 | 6/2001 | Boveja |
| 2002/0022873 A1 | 2/2002 | Erickson et al. |
| 2002/0055779 A1 | 5/2002 | Andrews |
| 2002/0099256 A1 | 7/2002 | Manne |
| 2002/0099419 A1 | 7/2002 | Cohen et al. |
| 2002/0161415 A1 | 10/2002 | Cohen et al. |
| 2002/0193859 A1 | 12/2002 | Schulman et al. |
| 2003/0004546 A1 | 1/2003 | Casey |
| 2003/0045909 A1 | 3/2003 | Gross et al. |
| 2003/0045914 A1 | 3/2003 | Cohen et al. |
| 2003/0050677 A1 | 3/2003 | Gross et al. |
| 2003/0083698 A1 | 5/2003 | Whitehurst et al. |
| 2003/0100933 A1 | 5/2003 | Ayal et al. |
| 2003/0114905 A1 | 6/2003 | Kuzma |
| 2003/0236557 A1 | 12/2003 | Whitehurst et al. |
| 2003/0236558 A1 | 12/2003 | Whitehurst et al. |
| 2004/0015205 A1 | 1/2004 | Whitehurst et al. |
| 2004/0034394 A1 | 2/2004 | Woods et al. |
| 2004/0172089 A1 | 9/2004 | Whitehurst et al. |
| 2004/0243182 A1 | 12/2004 | Cohen et al. |
| 2004/0243185 A1 | 12/2004 | Weiss et al. |

FOREIGN PATENT DOCUMENTS

| | | |
|---|---|---|
| WO | WO-98/43700 A1 | 10/1998 |
| WO | WO-98/43701 A1 | 10/1998 |
| WO | WO-01/60445 A2 | 8/2001 |
| WO | WO-01/60445 A3 | 8/2001 |
| WO | WO-01/76690 A1 | 10/2001 |
| WO | WO-02/058782 A2 | 8/2002 |
| WO | WO-02/058782 A3 | 8/2002 |
| WO | WO-02/068042 A1 | 9/2002 |
| WO | WO-02/092165 A1 | 11/2002 |
| WO | WO-03/018113 | 3/2003 |
| WO | WO-03/018113 A1 | 3/2003 |

OTHER PUBLICATIONS

Barker, et al., "Determination of the Distribution of Conduction Velocities in Human Nerve Trunks," Biomedical Engineering, vol. 26(2), (1979), pp. 76-81.

Bilgutay, et al., "Vagal Tuning: A New Concept in the Treatment of Supraventricular Arrhythmias, Angina Pectoris, and Heart Failure," Journal of Thoracic and Cardiovascular surgery, vol. 56, No. 1 (Jul. 1968), pp. 71-82.

Cameron, et al., "Micromodular Implants to Provide Electrical Stimulation of Paralyzed Muscles and Limbs," IEEE Transactions on Biomedical Engineering, vol. 44, No. 9 (Sep. 1997), pp. 781-790.

Grill, et al., "Stimulus Waveforms for Selective Neural Stimulation," IEEE Engineering in Medicine and Biology, Jul./Aug. 1995, pp. 375-385.

Lesser, et al., "Unexpected Places—How did Vagus Nerve Stimulation Become a Treatment for Epilepsy?" Neurology, vol. 52 (1999), pp. 1117-1118.

Schoonhoven, et al., "The Inverse Problem in Electroneurography-I: Conceptual Basis and Mathematical Formulation," Biomedical Engineering, vol. 35(10), (1988), pp. 769-777.

Sweeney, et al., "An Asymmetric Two Electrode Cuff for Generation of Unidirectionally Propagated Action Potentials," IEEE Transactions on Biomedical Engineering, vol. BME-33, No. 6 (Jun. 1986), pp. 541-549.

Ungar, et al., "Generation of Unidirectionally Propagating Action Potentials Using a Monopolar Electrode Cuff," Annals of Biomedical Engineering, vol. 14(5), (1986), pp. 437-450.

Uthman, et al., "Treatment of Epilepsy by Stimulation of the Vagus Nerve," Neurology, vol. 34(1), (1993), pp. 338-345.

Van Den Honert, et al., "A Technique far Collision Block of Peripheral Nerve: Frequency Dependence," IEEE Transactions on Biomedical Engineering, vol. BME-28, No. 5 (May 1981), pp. 379-382.

Van Den Honert, et al., "A Technique for Collision Block of Peripheral Nerve: single Stimulus Analysis," IEEE Transactions on Biomedical Engineering, vol. BME-28, No. 5 (May 1981), pp. 372-378.

Van Den Honert, et al., "Generation of Unidirectionally Propagated Action Potentials in a Peripheral Nerve by Brief Stimuli," Science, vol. 206 (Dec. 14, 1979), pp. 1311-1312.

Veraart, et al., "Selective Control of Muscle Activation with a Multipolar Nerve Cuff Electrode," IEEE Transactions on biomedical Engineering, vol. 40, No. 7 (Jul. 1993), pp. 640-653.

Official Communication, U.S. Appl. No. 10/178,050, mailed Aug. 11, 2005.

Official Communication, U.S. Appl. No. 10/178,050, mailed Aug. 29, 2006.
Official Communication, U.S. Appl. No. 10/178,050, mailed Jan. 29, 2007.
Official Communication, U.S. Appl. No. 10/178,050, mailed Mar. 13, 2008.
Official Communication, U.S. Appl. No. 10/178,050, mailed Jul. 28, 2008.
Official Communication, U.S. Appl. No. 10/178,050, mailed Jan. 6, 2009.
Official Communication, U.S. Appl. No. 10/178,050, mailed Aug. 3, 2009.
Official Communication, U.S. Appl. No. 10/178,050, mailed Jan. 27, 2010.
Official Communication, U.S. Appl. No. 10/178,050, mailed May 3, 2010.
PCT Application No. PCT/US03/18506, filed Jun. 11, 2003, International Search Report.

* cited by examiner

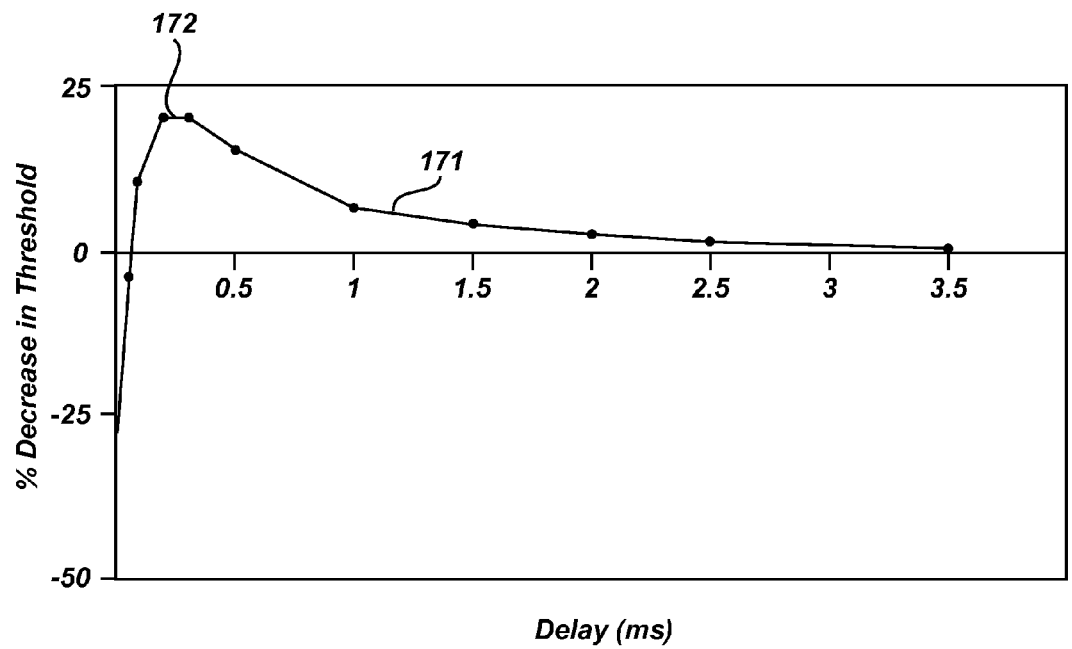
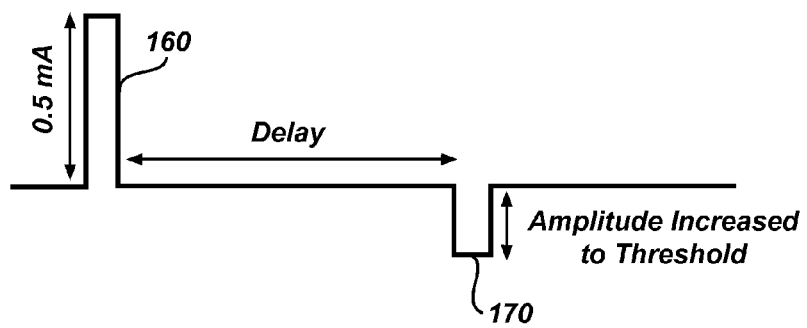
Fig. 7A

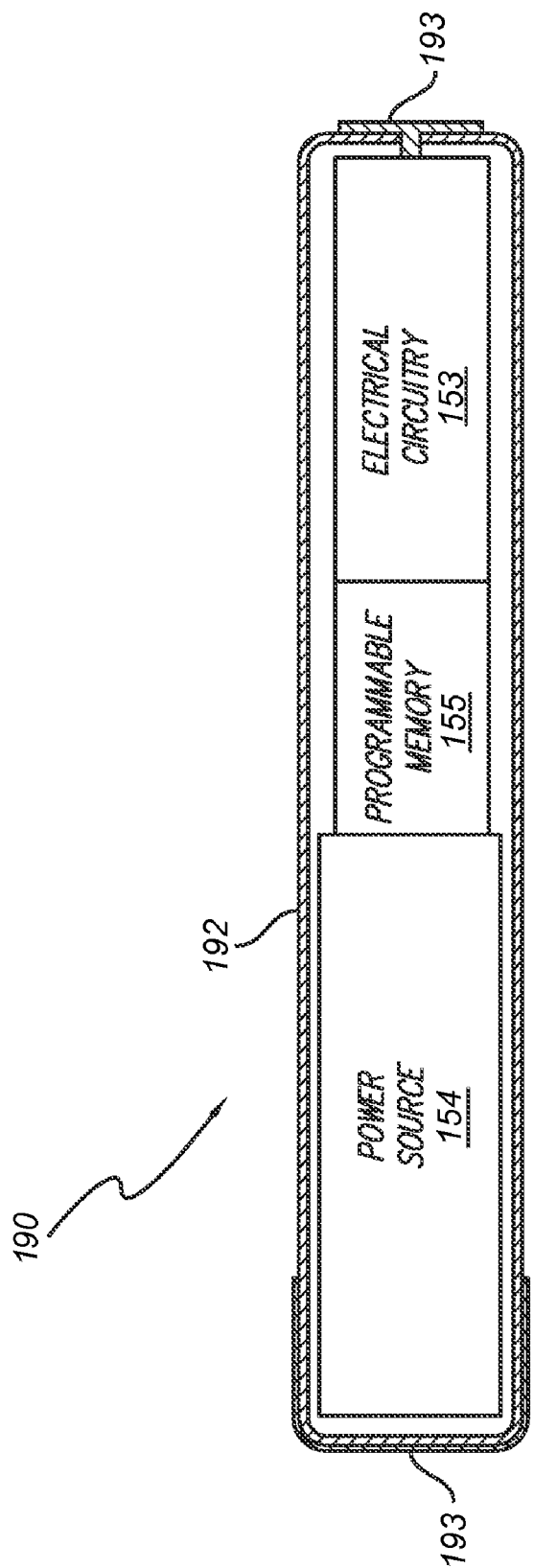

ENHANCEMENT OF NEURAL SIGNAL TRANSMISSION THROUGH DAMAGED NEURAL TISSUE VIA HYPERPOLARIZING ELECTRICAL STIMULATION CURRENT

BACKGROUND

There are many diseases, conditions, and syndromes where the propagation of neural signals via neurological pathways may be hindered or inhibited, such as nerve compression syndromes, nerve ischemia/infarct, radiation-induced injury, inflammation, and degeneration. Nerve compression (including neurapraxia and axontmesis) is one of the most common problems that affects neuronal structures. Nerve compression can affect distal nerve segments, as occurs in tarsal tunnel syndrome, carpal tunnel syndrome, or peroneal neuropathy at the fibular neck, but is even more common proximally where a herniated disc may compress a spinal nerve root.

Nerve compression may result from direct external pressure or contusion related to trauma, work, hobbies, or sports activities. Additionally or alternatively, nerve compression may be caused by structural abnormalities within the body. The exact mechanism of nerve compression is not completely understood and may include varying degrees of friction and ischemia.

Clinical manifestations of nerve compression include pain, which may be sharp or burning, and paresthesia. In more severe cases, there may be weakness distal to the site of compression. Physical symptoms of nerve compression include muscle atrophy, weakness, and involuntary twitching of muscle fibers. A person's reflexes may also be affected, depending on the site of the compression. Pain associated with nerve compression is often intensified during sleep.

One of the more common nerve compression syndromes is carpal tunnel syndrome (CTS), which affects millions of Americans and results in billions of dollars of workers compensation claims every year. In CTS, the median nerve is compressed at the wrist and often results in tingling, numbness, sleep disruption, coldness, weakness, and pain. Most cases of CTS are idiopathic. While repetitive activities are often blamed for the development of CTS, the correlation is often unclear. Physiology and family history may also play a role in an individual's susceptibility to CTS.

Various treatment therapies have been used to treat or curtail the occurrence of CTS and other nerve compression syndromes. For example, immobilizing braces, massages, ultrasonic therapy, localized steroid injections, and anti-inflammatory drugs such as ibuprofen or aspirin have all been used with varying levels of success. Severe cases of nerve compression can sometimes be remedied through surgical procedures. For example, CTS may be alleviated through a surgical procedure in which the transverse carpal ligament is cut to relieve pressure from the compressed median nerve. However, each of these treatment therapies can be ineffective, offer only temporary relief, or cause other undesirable side effects.

SUMMARY

Methods of enhancing transmission of a neural signal through damaged neural tissue include providing a stimulator, programming the stimulator with one or more stimulation parameters configured to enhance transmission of a neural signal through the damaged neural tissue, and applying a hyperpolarizing electrical stimulation current with the stimulator to the damaged neural tissue in accordance with the one or more stimulation parameters.

Systems for enhancing transmission of a neural signal through damaged neural tissue include a stimulator configured to be implanted at least partially within a patient and to generate a hyperpolarizing electrical stimulation current in accordance with one or more stimulation parameters adjusted to enhance transmission of the neural signal through the damaged neural tissue, a programmable memory unit in communication with the stimulator and programmed to store the one or more stimulation parameters to at least partially define the hyperpolarizing electrical stimulation current such that the hyperpolarizing electrical stimulation current is configured to enhance the transmission of the neural signal transmission through the damaged neural tissue, and means, operably connected to the stimulator, for applying the hyperpolarizing electrical stimulation current to the damaged neural tissue.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 7A shows the results of an experiment wherein the hyperpolarizing pulse of FIG. 6A and a subsequent depolarizing pulse are applied to a cell membrane within damaged neural tissue according to principles described herein.

FIG. 9 illustrates an exemplary microstimulator according to principles described herein.

Throughout the drawings, identical reference numbers designate similar, but not necessarily identical, elements.

DETAILED DESCRIPTION

Methods and systems for enhancing transmission of a neural signal through damaged neural tissue are described herein. A stimulator is configured to apply hyperpolarizing electrical stimulation current to the damaged neural tissue in accordance with one or more stimulation parameters. The hyperpolarizing electrical stimulation is configured to enhance neural signal transmission by controlling the operation of one or more voltage-gated sodium channels within the damaged neural tissue. As used herein, the term "enhancing neural signal transmission" and variations thereof refer to allowing, improving, enabling, and/or otherwise facilitating transmission of one or more neural signals through neural tissue that has been damaged by disease and/or injury.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
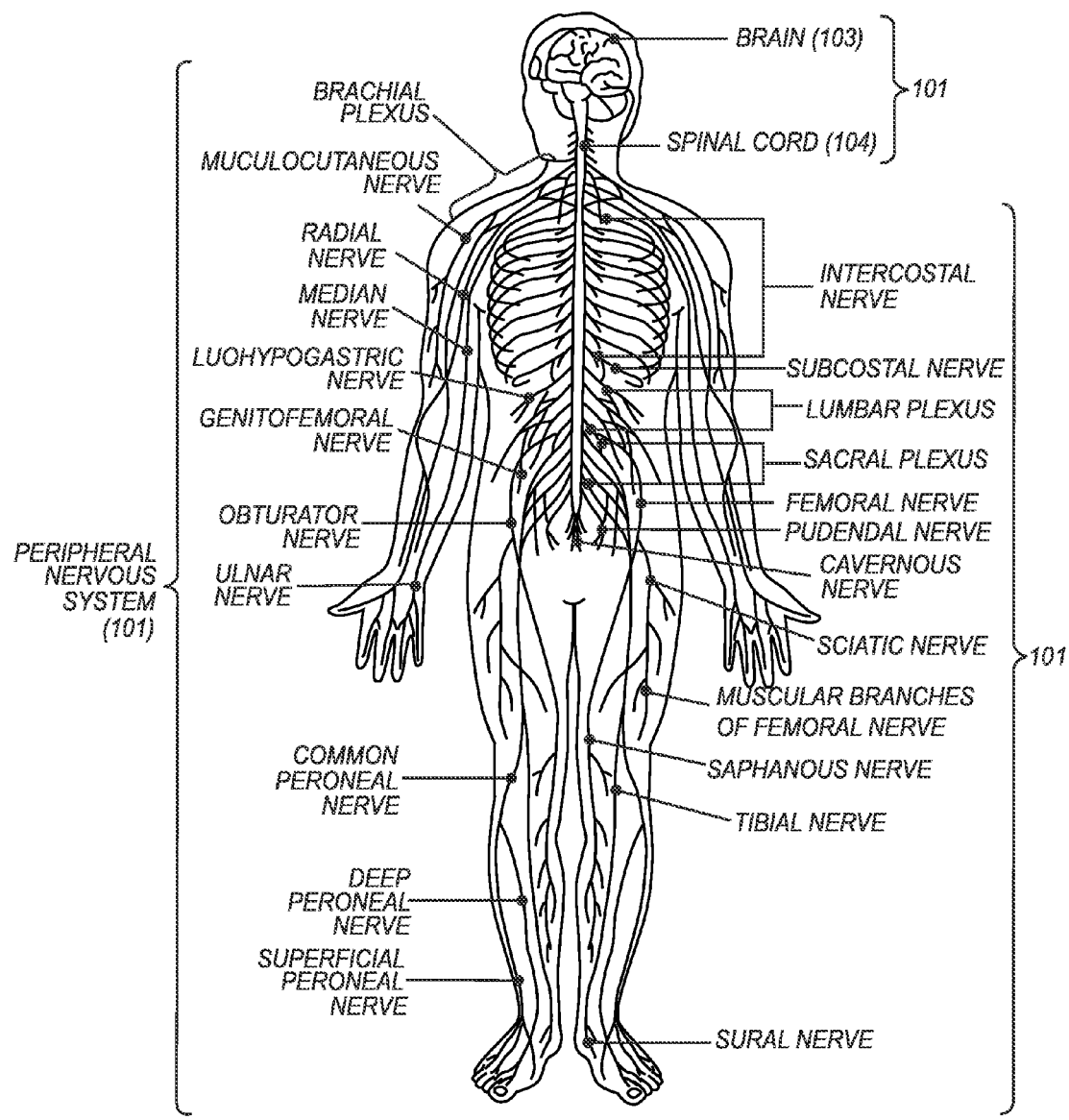
FIG. 1 is a diagram of the human nervous system.

Medical conditions that impede propagation of neural signals may affect many different nerves throughout the body. Hence, before discussing the present methods and systems for enhancing neural signal transmission, a brief overview of the human nervous system will be given. FIG. 1 is a diagram of the human nervous system. The nervous system is divided into a central nervous system 100 and a peripheral nervous system 101. The central nervous system 100 includes the brain 102 and the spinal cord 103. The peripheral nervous system 101 includes a number of nerves that branch from various regions of the spinal cord 103. For example, the peripheral nervous system 101 includes, but is not limited to, the brachial plexus, the musculocutaneous nerve, the radial nerve, the median nerve, the iliohypogastric nerve, the genitofemoral nerve, the obturator nerve, the ulnar nerve, the peroneal nerve, the sural nerve, the tibial nerve, the saphenous nerve, the femoral nerve, the sciatic nerve, the cavernous nerve, the pudendal nerve, the sacral plexus, the lumbar plexus, the subcostal nerve, and the intercostal nerves.

The peripheral nervous system 101 may be further divided into the somatic nervous system and the autonomic nervous system. The somatic nervous system is the part of the peripheral nervous system 101 associated with the voluntary control of body movements through the action of skeletal muscles. The somatic nervous system consists of afferent fibers which receive information from external sources, and efferent fibers which are responsible for muscle contraction. The autonomic nervous system, on the other hand, regulates the involuntary action of various organs.

Figure 2A:
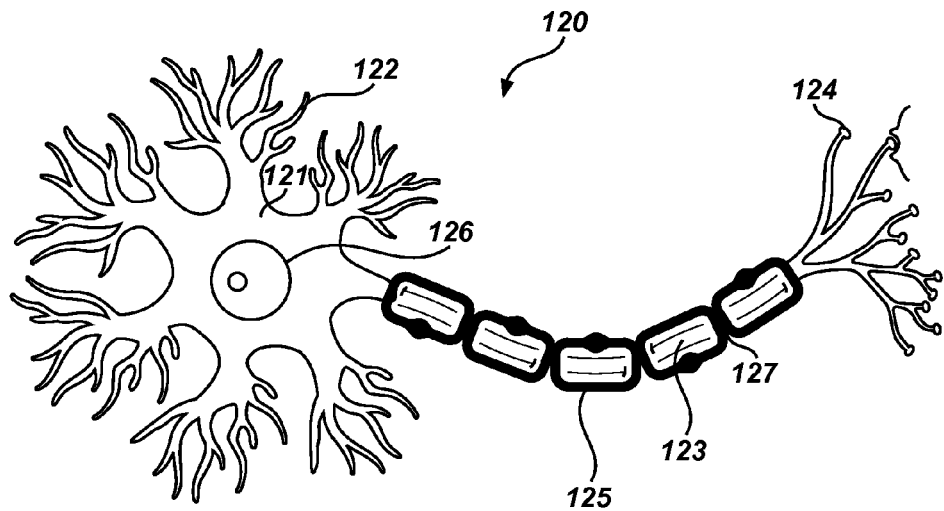
FIG. 2A illustrates an exemplary neuron.

A nerve is composed of a number of neurons, which are electrically excitable cells that process and transmit information. FIG. 2A illustrates an exemplary neuron 120. As shown in FIG. 2A, a neuron 120 includes a soma or cell body 121, a number of dendrites 122, an axon 123, axon terminals 124, and sheaths of myelin 125 along the axon 123. Each of these components will now be described in more detail.

The soma 121 is the central part of the neuron 120 and includes the nucleus 126 of the cell. The dendrites 122 are tree-like extensions configured to form synaptic contacts with terminals of other neurons to facilitate transmission of nerve impulses. The axon 123 is a cable-like projection which extends from the soma 121. The axon 123 carries neural signals to and from the soma 121. The axon terminals 124 are specialized structures at the end of the axon 123 that are used to release neurotransmitter chemicals and communicate with target neurons.

Figure 2B:
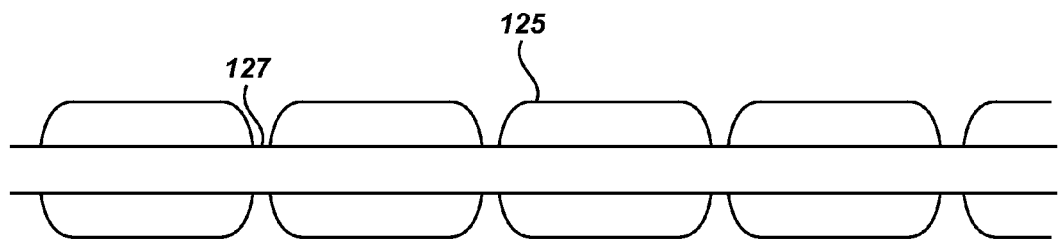
FIG. 2B is a cross sectional side view of the axon of a neuron.

To minimize metabolic expense while maintaining rapid conduction, many neurons have insulating sheaths of myelin 125 around their axons 123. The myelin 125 is formed by glial cells: oligodendrocytes in the central nervous system and Schwann cells in the peripheral nervous system. The myelin sheath enables action potentials (described in more detail below) to efficiently propagate along the axon 123. The myelin sheath 125 is punctuated by unsheathed nodes, referred to as nodes of Ranvier 127. These nodes of Ranvier 127 contain a high density of voltage-gated sodium channels, which will be described in more detail below. The myelin 125 and nodes of Ranvier 127 are illustrated in more detail in the cross sectional side view of FIG. 2B.

Each neuron 120 is surrounded by a cell membrane, which is a semipermeable lipid bilayer common to all living cells. The cell membrane physically separates the intracellular components of the neuron from the extracellular environment and is configured to regulate what enters and exits the cell.

An electrical voltage, or potential difference, always exists between the inside and outside of a normal cell membrane. This voltage is often referred to as the transmembrane potential and results from the distribution of ions across the cell membrane and from the permeability of the membrane to these ions. Hence, normal cell membranes are electrically excitable.

The electrical excitability of cell membranes enables neurons to communicate via chemical and electrical synapses in a process known as synaptic transmission. The fundamental process that triggers synaptic transmission is the action potential, which is a signal generated by electrically exciting the cell membrane of a neuron.

Figure 3:
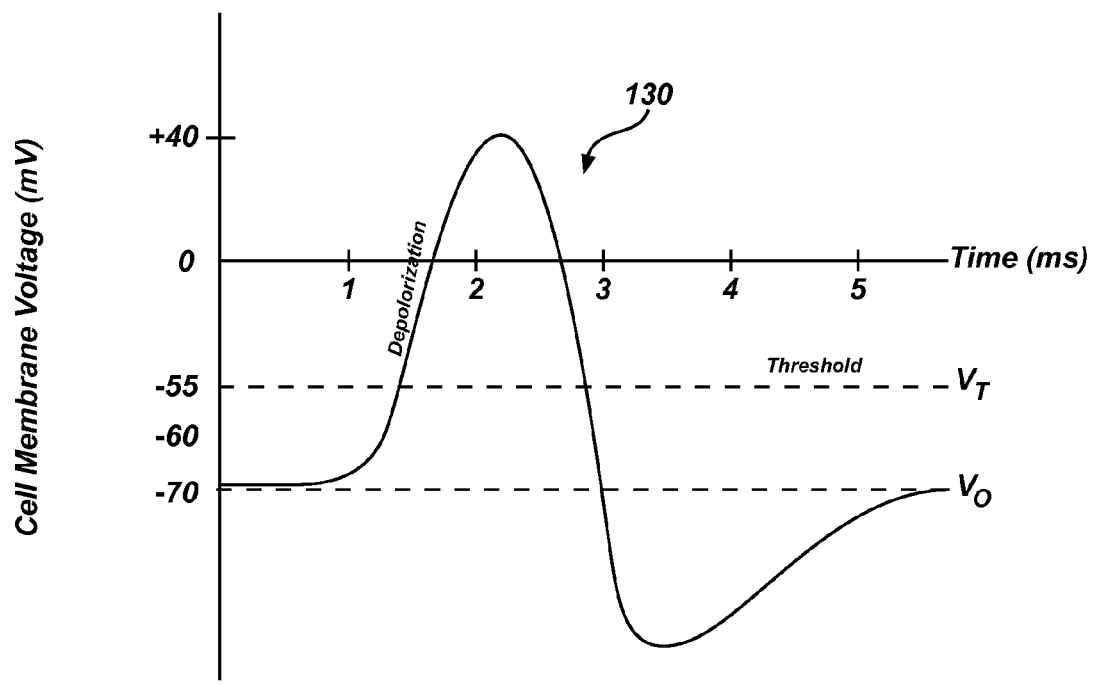
FIG. 3 shows a graph of an action potential as it passes a point on a cell membrane according to principles described herein.

FIG. 3 shows a graph of an action potential 130 as it passes a point on a cell membrane. As shown in FIG. 3, in the absence of excitation, the nerve cell membrane has a resting potential or voltage $V_0$. The resting potential of the cell membrane is −70 mV in FIG. 3 for illustrative purposes only and may vary from cell to cell. When the cell is excited with an inward current, the cell membrane depolarizes (i.e., the transmembrane potential becomes more positive). If the cell membrane depolarizes above a threshold potential $V_T$, the cell will fire or generate an action potential wherein the voltage of the cell membrane rapidly swings in polarity from negative to positive and back.

For example, the threshold potential $V_T$ for the cell membrane shown in FIG. 3 is −55 mV. If the cell membrane depolarizes above this point, the voltage of the cell membrane rapidly increases until it peaks at about +40 mV. The voltage of the cell membrane then rapidly decreases and swings below the resting potential $V_0$. The cell membrane voltage then gradually returns to the resting potential $V_0$.

It will be recognized that the threshold potential $V_T$ is dependent on the state of non-linear ion gates that make a particular nerve cell excitable. Each of the ion gates may be in different states.

Hence, an action potential is a rapid swing in the polarity of the cell membrane voltage from negative to positive and back. The entire cycle may only last a few milliseconds. Action potentials can propagate or travel for long distances along a nerve axon and are used to carry neural signals between various parts of the body and the spinal cord.

As mentioned, there is an initial inwards current during the depolarization phase of an action potential in excitable cells. The initial inwards current is due at least in part to proteins called voltage-gated ion channels that are embedded within the cell membrane at the nodes of Ranvier. These voltage-gated ion channels are configured to allow a particular type of ion to pass therethrough and into the inner portion of the cell.

One type of voltage-gated ion channel is known as a voltage-gated sodium channel (VGSC). A voltage-gated sodium channel is configured to allow sodium ions to pass through to the inner portion of the cell. As the name suggests, voltage-dependent sodium channels are voltage dependent—i.e., their conformations change as the voltage across the cell membrane changes.

Figure 4:
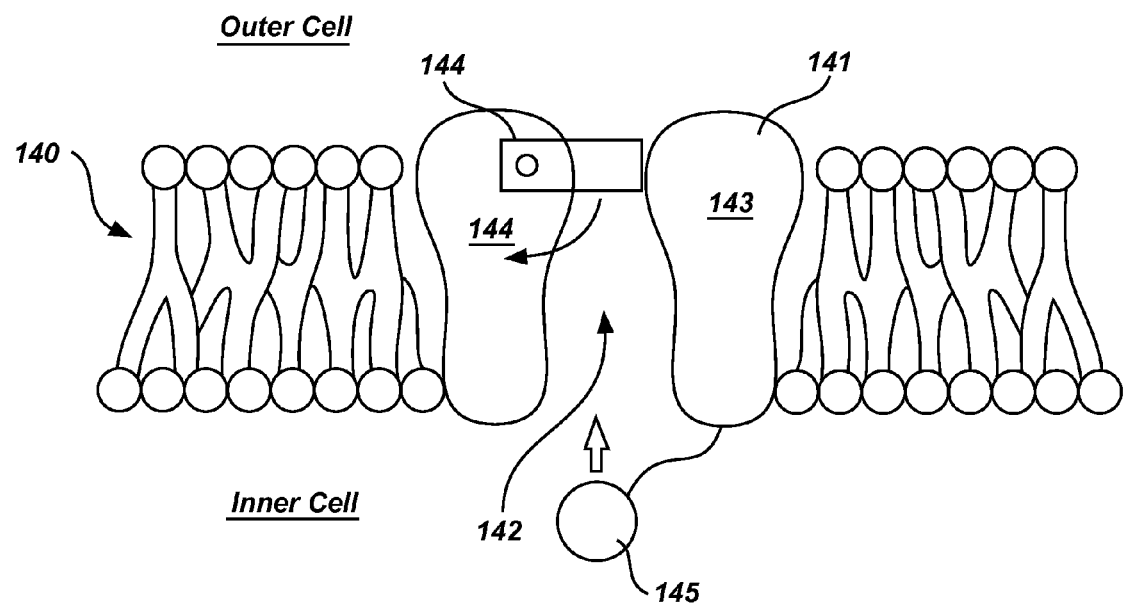
FIG. 4 is a cross sectional side view of an exemplary cell membrane with a voltage-gated sodium channel (VGSC) embedded therein according to principles described herein.

To illustrate, FIG. 4 is a cross sectional side view of an exemplary cell membrane 140 with a VGSC 141 embedded therein. It will be recognized that a typical cell membrane 140 includes multiple VGSCs 141. However, a single VGSC 141 is shown in FIG. 4 for illustrative purposes only.

As shown in FIG. 4, the VGSC 141 includes a protein substance 143 surrounding a channel 142 that extends from the outer to the inner portion of the cell. The VGSC 141 also includes two gates configured to regulate the opening and closing of the channel 142: an m-gate 144 and an h-gate 145. Both the m and h gates 144 and 145 must be open for current to flow through the channel. The m-gate 144 is a relatively fast acting gate, while the h-gate 145 is a relatively slow acting gate.

When the transmembrane voltage is at a rest potential, the probability that an m-gate 144 is open is low and the probability that an h-gate 145 is open is relatively high (e.g., 60%). In the closed state, the m-gate 144 prevents sodium ions from getting through the channel 141. It will be recognized, however, that because of thermodynamic and probabilistic factors, not all m-gates are closed at the rest potential, and a given channel may switch between states.

During the depolarization phase of an action potential, the transmembrane potential becomes more positive. An increase in the transmembrane potential causes the probability of an m-gate 145 being open to rise rapidly. Sodium ions then enter the channel 141. The influx of sodium ions into the channel 141 causes the transmembrane potential to increase even more, and this feed forward process causes further depolarization and transfer of the depolarization of the cell membrane along the axon in both directions.

As the transmembrane potential increases, the probability of the h-gate 145 being open will decrease (i.e., more h-gates will be in the closed state at a given time). The change in probability of the h-gate 145 being in the open state has a slower time constant than the time constant of the change of the probability of the m-gate 144 being in an open state. When a given h-gate 145 is closed, it prevents additional sodium ions from getting through that channel 141.

Hence, the action of the m and h gates 144 and 145 of VGSCs enable the propagation of action potentials along the axon of a neuron. Action potentials travel relatively fast and efficiently along axons due to the low capacitance of the myelinated sections. However, in axons that become demyelinated due to medical conditions such as disease or injury, the VGSCs described above may spread out along the axon. The combination of VGSC spreading and an increased capacitance (due to demyelination) leads to the need for increased charge density within the axon to propagate an action potential. However, the body may not be able to produce such an increased inward current. Hence, neural signals that are encoded by or in the form of action potentials may be slowed or impeded when they reach a damaged portion of an axon.

Examples of medical conditions that may impede or block neural signal transmission include, but are not limited to, nerve compression syndromes (e.g., carpal tunnel syndrome, cubital tunnel syndrome, radial tunnel syndrome, pronator syndrome, high radial nerve palsy, lateral antebrachial cutaneous nerve entrapment syndrome, meralgia paresthetica, tarsal tunnel syndrome, thoracic outlet syndrome, trigeminal neuralgia, etc.), nerve ischemia/infarct, radiation-induced injury, inflammation, degeneration, and diseases of the nervous system (e.g., multiple sclerosis and Guillain-Barre syndrome).

As will be described in more detail below, it is believed that an electrical stimulation current may be applied to neural tissue that no longer has the ability to effectively generate and/or propagate action potentials in order to enhance transmission of neural signals along the damaged neural tissue. In some examples, as will be described in more detail below, the electrical stimulation current is configured to regulate the operation of one or more VGSCs 141 within a neuron.

Consequently, a stimulator may be implanted within a patient to deliver an electrical stimulation current to damaged neural tissue in order to enhance neural signal transmission within the damaged neural tissue. Additionally or alternatively, the stimulation current may be provided by a stimulator located external to the patient. However, it will be assumed in the examples given herein that the stimulation current is provided by an implantable stimulator.

As used herein, and in the appended claims, the term "stimulator" will be used broadly to refer to any device that delivers an electrical stimulation current to damaged neural tissue to enhance neural signal transmission. Thus, the term "stimulator" includes, but is not limited to, a microstimulator, implantable pulse generator (IPG), spinal cord stimulator (SCS), system control unit, external trial stimulator, or similar device. Moreover, as used herein, the term "damaged neural tissue" refers to any neural tissue that no longer has the ability to effectively generate and/or propagate action potentials.

Figure 5:
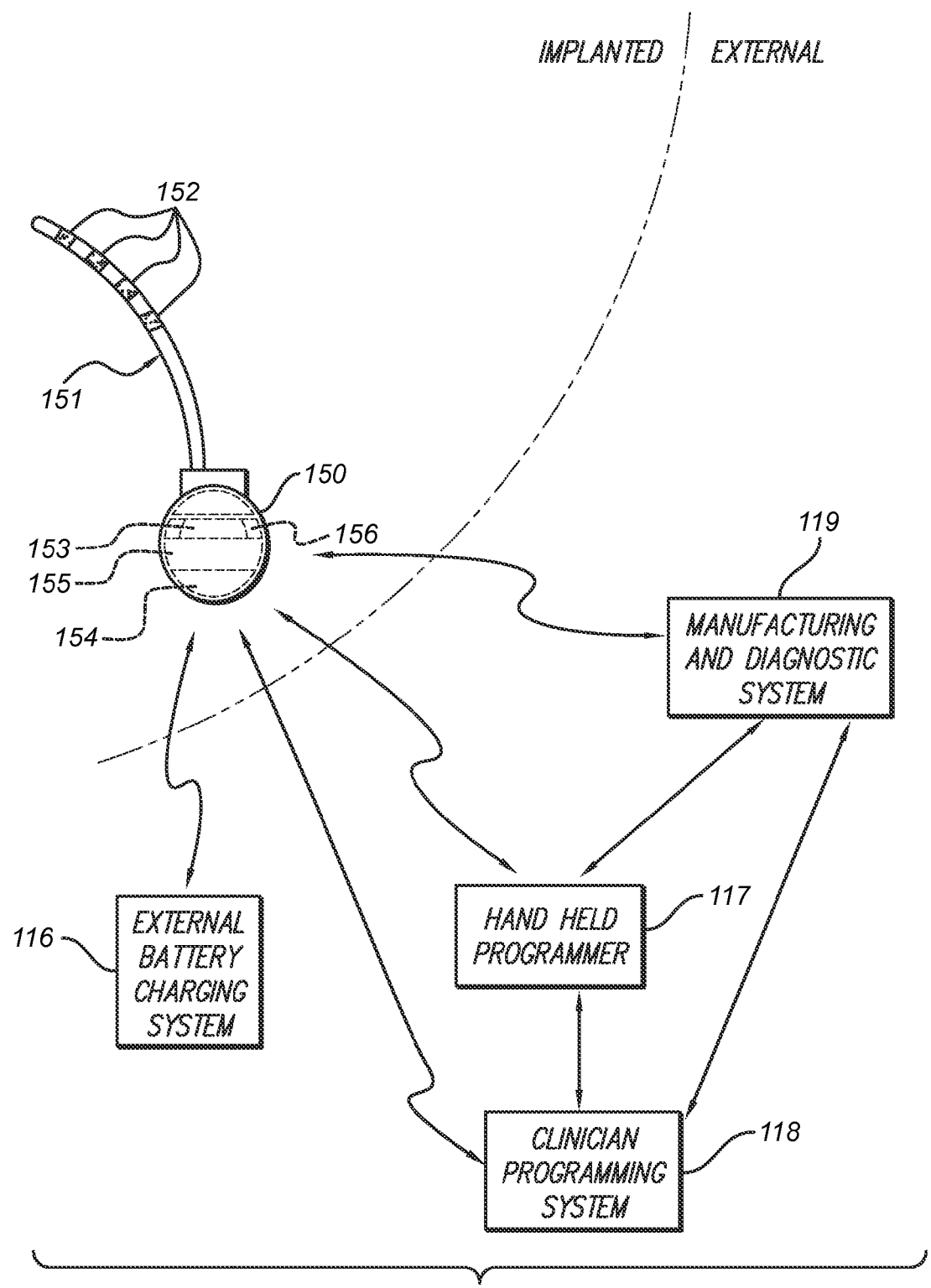
FIG. 5 illustrates an exemplary stimulator that may be used to apply electrical stimulation to damaged neural tissue to enhance neural signal transmission therethrough according to principles described herein.

To facilitate an understanding of the methods of delivering electrical stimulation to damaged neural tissue to enhance neural signal transmission that are described herein, a more detailed description of an implantable stimulator and its operation will now be given. FIG. 5 illustrates an exemplary stimulator 150 that may be used to apply electrical stimulation to damaged neural tissue to enhance neural signal transmission therethrough.

In some examples, the exemplary stimulator 150 shown in FIG. 5 may include at least one lead 151 coupled thereto. In some examples, the at least one lead 151 includes a number of electrodes 152 through which electrical stimulation current may be applied to damaged neural tissue. It will be recognized that the at least one lead 151 may include any number of electrodes 152 arranged in any configuration as best serves a particular application. In some alternative examples, as will be described in more detail below, the stimulator 150 is leadless.

As illustrated in FIG. 5, the stimulator 150 includes a number of components. It will be recognized that the stimulator 150 may include additional and/or alternative components as best serves a particular application. A power source 154 is configured to output voltage used to supply the various components within the stimulator 150 with power and/or to generate the power used for electrical stimulation. The power source 154 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), or the like.

In some examples, the power source 154 may be recharged using an external charging system. One type of rechargeable power supply that may be used is described in U.S. Pat. No. 6,596,439, which is incorporated herein by reference in its entirety. Other battery construction techniques that may be used to make the power source 154 include those shown, e.g., in U.S. Pat. Nos. 6,280,873; 6,458,171; 6,605,383; and 6,607,843, all of which are incorporated herein by reference in their respective entireties.

The stimulator 150 may also include a coil 158 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 154.

For example, an external battery charging system (EBCS) 116 may be provided to generate power that is used to recharge the power source 154 via any suitable communication link. Additional external devices including, but not limited to, a hand held programmer (HHP) 117, a clinician programming system (CPS) 118, and/or a manufacturing and diagnostic system (MDS) 119 may also be provided and configured to activate, deactivate, program, and/or test the stimulator 150 via one or more communication links. It will be recognized that the communication links shown in FIG. 5 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 150. It will be recognized that any suitable communication link may be used among the various devices illustrated.

The external devices shown in FIG. 5 are merely illustrative of the many different external devices that may be used in connection with the stimulator 150. Furthermore, it will be recognized that the functions performed by any two or more of the external devices shown in FIG. 5 may be performed by a single external device.

The stimulator 150 may also include electrical circuitry 153 configured to generate the electrical stimulation current that is delivered to the damaged neural tissue via one or more of the electrodes 152. For example, the electrical circuitry 153 may include one or more processors, capacitors, integrated circuits, resistors, coils, and/or any other component configured to generate electrical stimulation current.

The stimulator 150 may also include a programmable memory unit 155 configured to store one or more stimulation parameters. The programmable memory unit 155 allows a patient, clinician, or other user of the stimulator 150 to adjust the stimulation parameters such that the stimulation applied by the stimulator 150 is safe and effective in treating a particular patient. The programmable memory unit 155 may include any type of memory unit such as, but not limited to, random access memory (RAM), static RAM (SRAM), a hard drive, or the like.

The stimulation parameters may control various parameters of the stimulation current applied to damaged neural tissue including, but not limited to, the frequency, pulse width, amplitude, waveform, electrode configuration (i.e., anode-cathode assignment), burst pattern (e.g., continuous or intermittent), duty cycle or burst repeat interval, ramp on time, and ramp off time.

Specific stimulation parameters may have different effects on different damaged neural tissue within a patient. Thus, in some embodiments, the stimulation parameters may be adjusted as best serves the particular patient being treated.

For example, the parameters may be configured so that the electrical stimulation current is in the form of a hyperpolarizing signal. As used herein, the term "hyperpolarizing signal" and variations thereof will refer to an electrical stimulation signal that causes the transmembrane potential to become more negative.

To understand how a hyperpolarizing signal may enhance neural signal transmission in neurons, it will be noted that under normal (i.e., healthy) resting conditions, only about 70% of the VGSC channels in any given neuron are in an activatable state. As will be described in more detail below, a hyperpolarizing signal may effectively increase this percentage and thereby increase the likelihood that an action potential will be generated by increasing the time that the h-gates 145 of the VGSCs 141 within a neuron remain open. An increase in the time that the h-gates 145 are open increases the likelihood that an action potential will be generated and that a neural signal encoded by the action potential will be transmitted by the neuron.

Figure 6A:
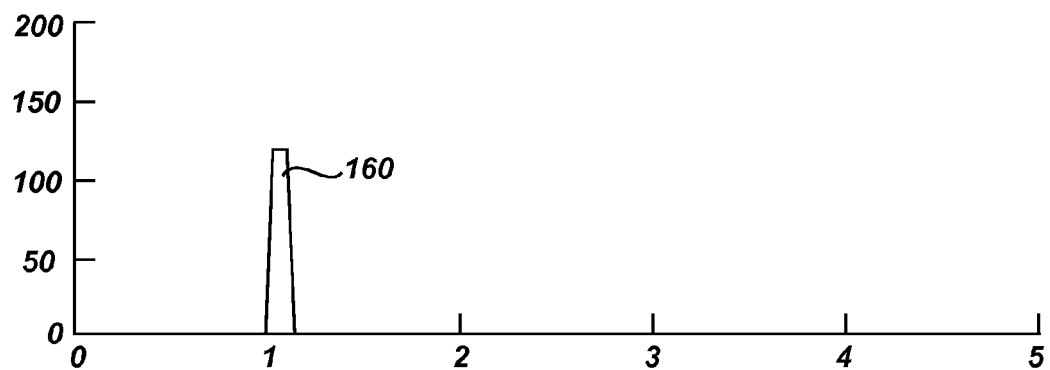
FIG. 6A illustrates an exemplary hyperpolarizing signal that may be applied to damaged neural tissue in order to enhance neural signal transmission therethrough according to principles described herein.

FIG. 6A illustrates an exemplary hyperpolarizing signal 160 that may be applied to damaged neural tissue in order to enhance neural signal transmission therethrough. As shown in FIG. 6A, the hyperpolarizing signal 160 includes a relatively short duration high amplitude pulse followed by a period of no stimulation. The specific stimulation parameters corresponding to the hyperpolarizing signal 160 of FIG. 6A may vary as may serve the particular damaged neural tissue being treated. For example, the hyperpolarizing signal 160 may have any suitable frequency (e.g., substantially less than or equal to 10 kHz), pulse width (e.g., anywhere between 10 and 200 microseconds), and amplitude.

Figure 6B:
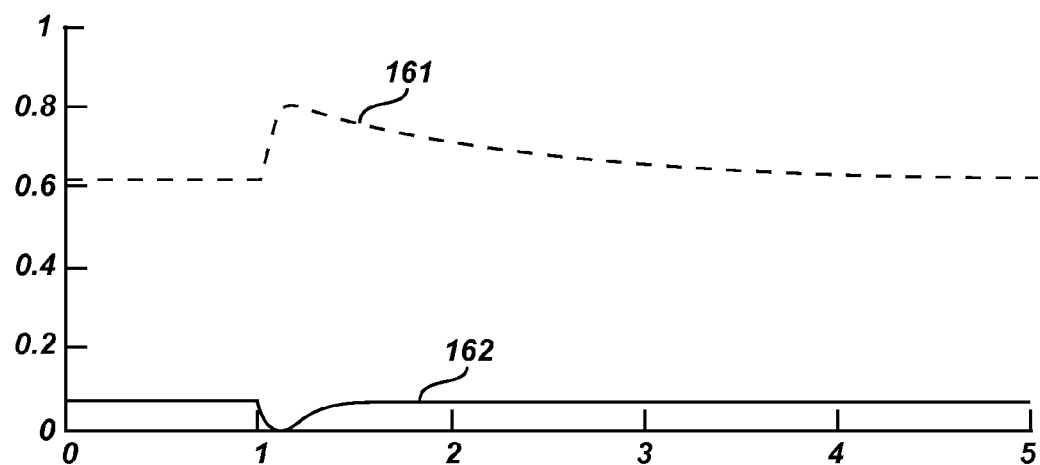
FIG. 6B is a graph of the probability of the h and m gates being open before, during, and after the hyperpolarizing pulse of FIG. 6A is applied to the damaged neural tissue according to principles described herein.

FIG. 6B is a graph of the probability of the h and m gates being open before, during, and after the hyperpolarizing pulse 160 is applied to the damaged neural tissue. The dotted line 161 represents the h-gates and the solid line 162 represents the m-gates. As shown in FIG. 6B, the h-gates are mostly open and the m-gates are mostly closed before the hyperpolarizing pulse 160 is applied. During the time in which the hyperpolarizing pulse 160 is applied to the damaged neural tissue, more h-gates open and more m-gates close, as shown in FIG. 6B.

After the hyperpolarizing pulse 160 has been applied, the number of h-gates that are open gradually decreases (i.e., some of the h-gates close), as shown by the relatively slow time constant of the dotted line 161 in FIG. 6B. The m-gates quickly go back to their resting potential state. Because more h-gates than normal are open during the period in which the h-gates are returning to their resting potential state, the damaged neural tissue is more excitable than normal, thereby increasing the likelihood that an action potential will be triggered by a subsequently applied depolarizing signal.

To illustrate the temporal effect of the hyperpolarizing pulse 160 on the threshold potential of a cell membrane, FIG. 7A shows the results of an experiment wherein the hyperpolarizing pulse 160 and a subsequent depolarizing pulse 170 are applied to a cell membrane within damaged neural tissue. In particular, the curve 171 shown in FIG. 7A represents the percent decrease in the threshold voltage of the cell membrane as a function of delay between the hyperpolarizing pulse 160 and the subsequent depolarizing pulse 170. Hence, the delay shown between the hyperpolarizing pulse 160 and the depolarizing pulse 170 corresponds to the values shown on the x-axis of the graph.

As shown in FIG. 7A, the threshold voltage of the cell membrane actually increases immediately after the hyperpolarizing pulse 160 is applied. This increase in threshold voltage is due to the fact that the m-gates initially close when the hyperpolarizing pulse 160 is applied, as described hereinabove with connection to FIGS. 6A-6B. However, the threshold voltage of the cell membrane quickly decreases and reaches a minimum (represented by peak 172 in FIG. 7A) a relatively short time after the hyperpolarizing pulse 160 is applied. At this point, the cell is more excitable than normal, and the amplitude of the depolarizing pulse 170 required to trigger an action potential is minimized.

As shown in FIG. 7A, the threshold voltage increases as the delay between the hyperpolarizing pulse 160 and the depolarizing pulse 170 increases. The increase in threshold voltage is due to the gradual closure of the h-gates after the hyperpolarizing pulse 160 is applied.

Figure 7B:
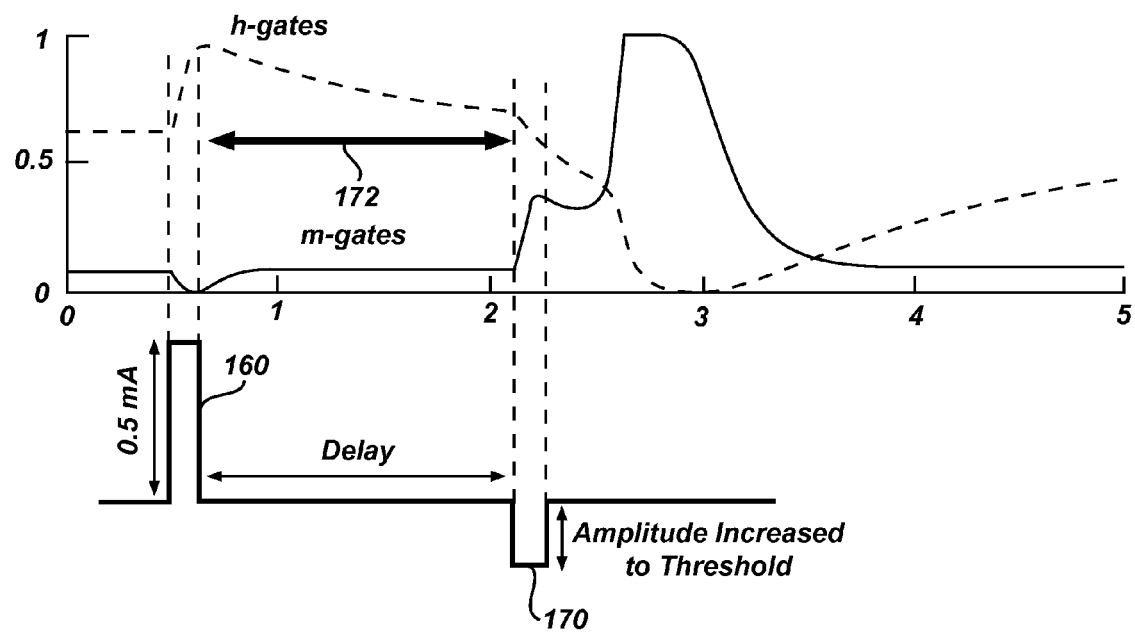
FIG. 7B illustrates the effect of the hyperpolarizing pulse of FIG. 6A and the subsequent depolarizing pulse of FIG. 7A on the probability of the h-gates and m-gates being open according to principles described herein.

FIG. 7B illustrates the effect of the hyperpolarizing pulse 160 and the subsequent depolarizing pulse 170 on the probability of the h-gates and m-gates being open. As shown in FIG. 7B, the h-gates open and the m-gates close during the time in which the hyperpolarizing pulse 160 is applied. The m-gates quickly return to their resting potential state while the h-gates slowly return to their resting potential state. During this period (represented by the horizontal arrow 172), the neural tissue is more excitable than normal. If the subsequent depolarizing pulse 170 has an amplitude sufficiently large to cause the m-gates to open, an action potential may be triggered.

Figure 8A:
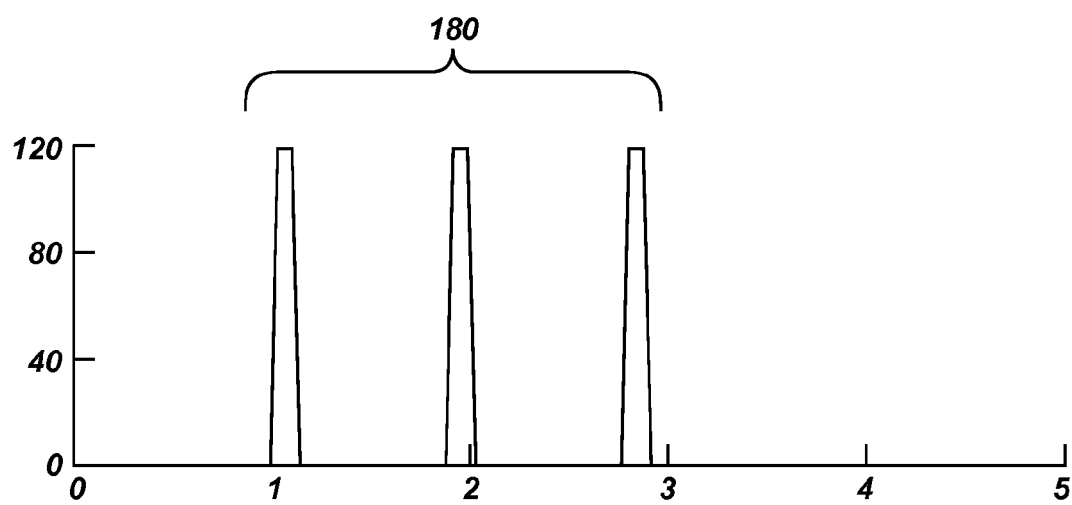
FIG. 8A illustrates another exemplary hyperpolarizing signal that may be applied to damaged neural tissue in order to enhance neural signal transmission therethrough according to principles described herein.
Figure 8B:
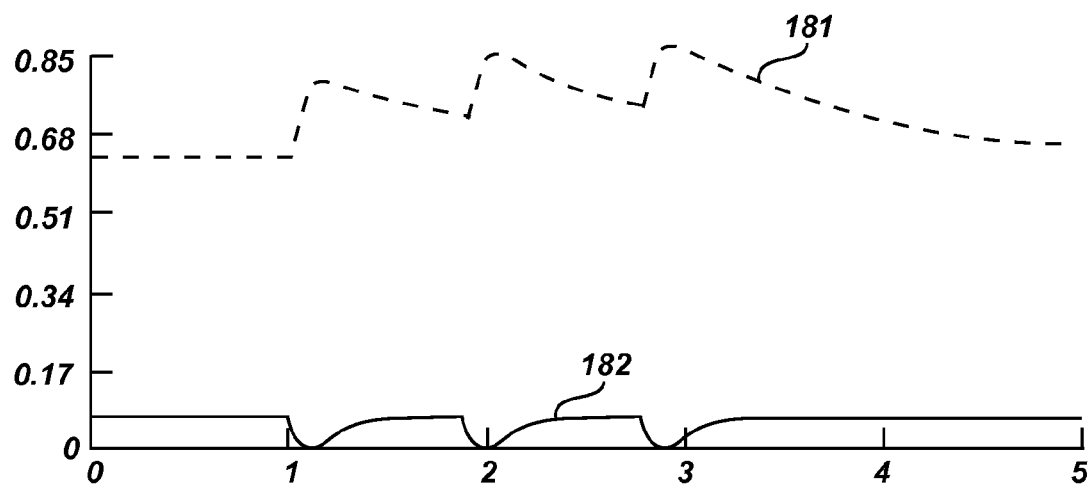
FIG. 8B is a graph illustrating the probability that the m-gates and the h-gates of the neural tissue are open as the hyperpolarizing signal of FIG. 8A is applied thereto according to principles described herein.

FIG. 8A illustrates an alternative hyperpolarizing signal 180 that may be applied to damaged neural tissue in order to enhance neural signal transmission therethrough. FIG. 8B is a graph illustrating the probability that the h-gates (dashed line 181) and the m-gates (solid line 182) of the neural tissue are open before, during, and after the hyperpolarizing signal 180 of FIG. 8A is applied thereto. As shown in FIG. 8A, the hyperpolarizing signal 180 includes a series of relatively brief stimulation pulses each followed by similarly brief periods of no stimulation. The effect of the hyperpolarizing periods on the h-gates will accrue and cause the h-gates to open. At the same time, the fast-acting m-gates will stay closed at the location of the hyperpolarizing stimulation, but may open on the fringes of the stimulation zone in response to the brief periods of stimulation. The combined effect of opening both the h-gates and the m-gates will increase the likelihood that an action potential will be triggered even when the incoming signal is weak.

The specific stimulation parameters corresponding to the hyperpolarizing signal 180 of FIG. 8A may vary as may serve the particular damaged neural tissue being treated. For example, the hyperpolarizing signal 180 may have any suitable frequency (e.g., substantially less than or equal to 10 kHz), pulse width (e.g., anywhere between 10 and 200 microseconds), and amplitude.

The stimulator 120 of FIG. 5 is illustrative of many types of stimulators that may be used in accordance with the systems and methods described herein. For example, the stimulator 120 may include an implantable pulse generator (IPG), a spinal cord stimulator (SCS), or any other type of implantable device configured to deliver electrical stimulation to damaged neural tissue within a patient. Exemplary IPGs suitable for use as described herein include, but are not limited to, those disclosed in U.S. Pat. Nos. 6,381,496, 6,553,263; and 6,760, 626. Exemplary spinal cord stimulators suitable for use as described herein include, but are not limited to, those disclosed in U.S. Pat. Nos. 5,501,703; 6,487,446; and 6,516,227. All of these listed patents are incorporated herein by reference in their respective entireties.

The stimulator 120 of FIG. 5 may alternatively include a microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

FIG. 9 illustrates an exemplary microstimulator 190 that may be used as the stimulator 150 described herein. Other configurations of the microstimulator 190 are possible, as shown in the above-referenced patents and as described further below.

As shown in FIG. 9, the microstimulator 190 may include the power source 154, the programmable memory 155, and the electrical circuitry 153 described in connection with FIG. 5. These components are housed within a capsule 192. The capsule 192 may be a thin, elongated cylinder or any other shape as best serves a particular application. The shape of the capsule 192 may be determined by the structure of the desired stimulation site and the method of implantation. In some examples, the microstimulator 190 may include two or more leadless electrodes 193 disposed on the outer surface thereof.

The external surfaces of the microstimulator 190 may advantageously be composed of biocompatible materials. For example, the capsule 192 may be made of glass, ceramic, metal, or any other material that provides a hermetic package that will exclude water vapor but permit passage of electromagnetic fields used to transmit data and/or power. The electrodes 193 may be made of a noble or refractory metal or compound, such as platinum, iridium, tantalum, titanium, titanium nitride, niobium or alloys of any of these, in order to avoid corrosion or electrolysis which could damage the surrounding tissues and the device.

Figure 10A:
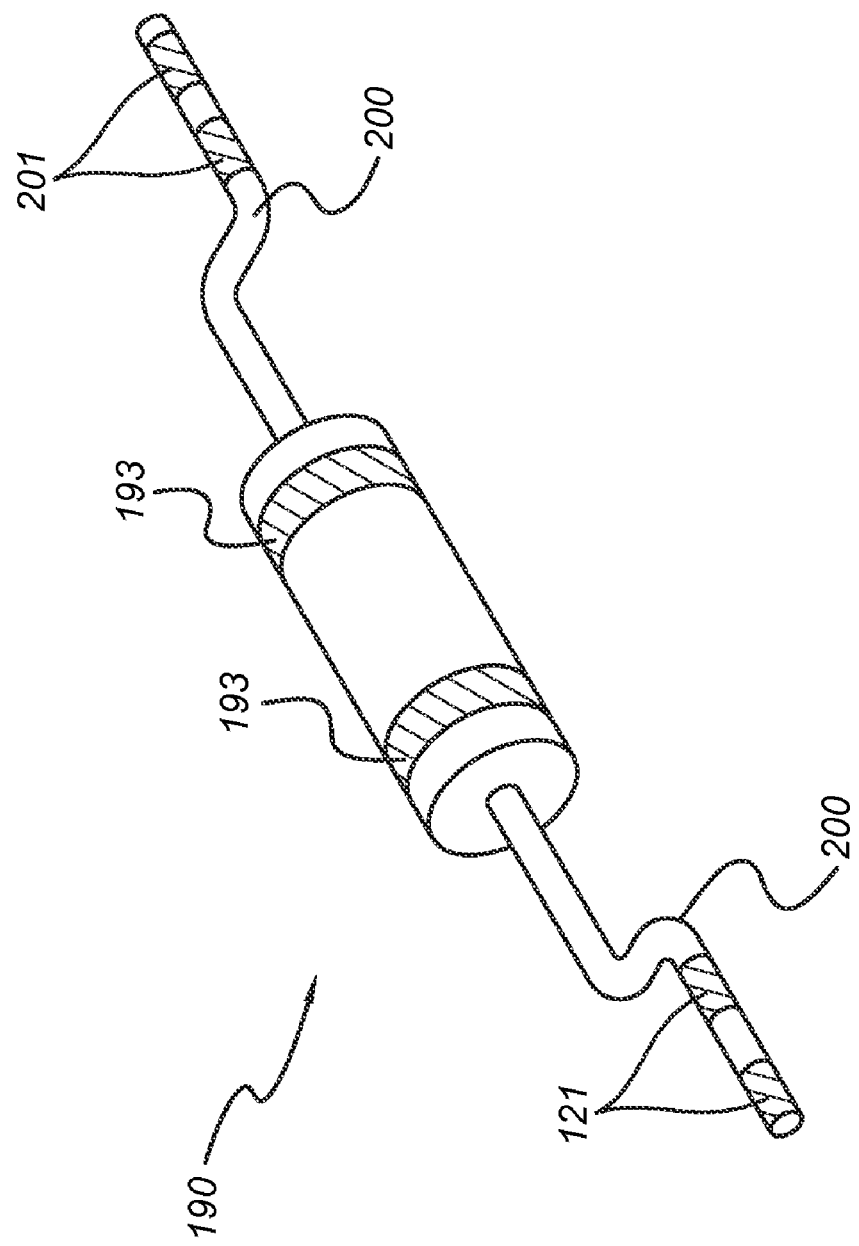
FIG. 10A shows an example of a microstimulator with one or more leads coupled thereto according to principles described herein.
Figure 10B:
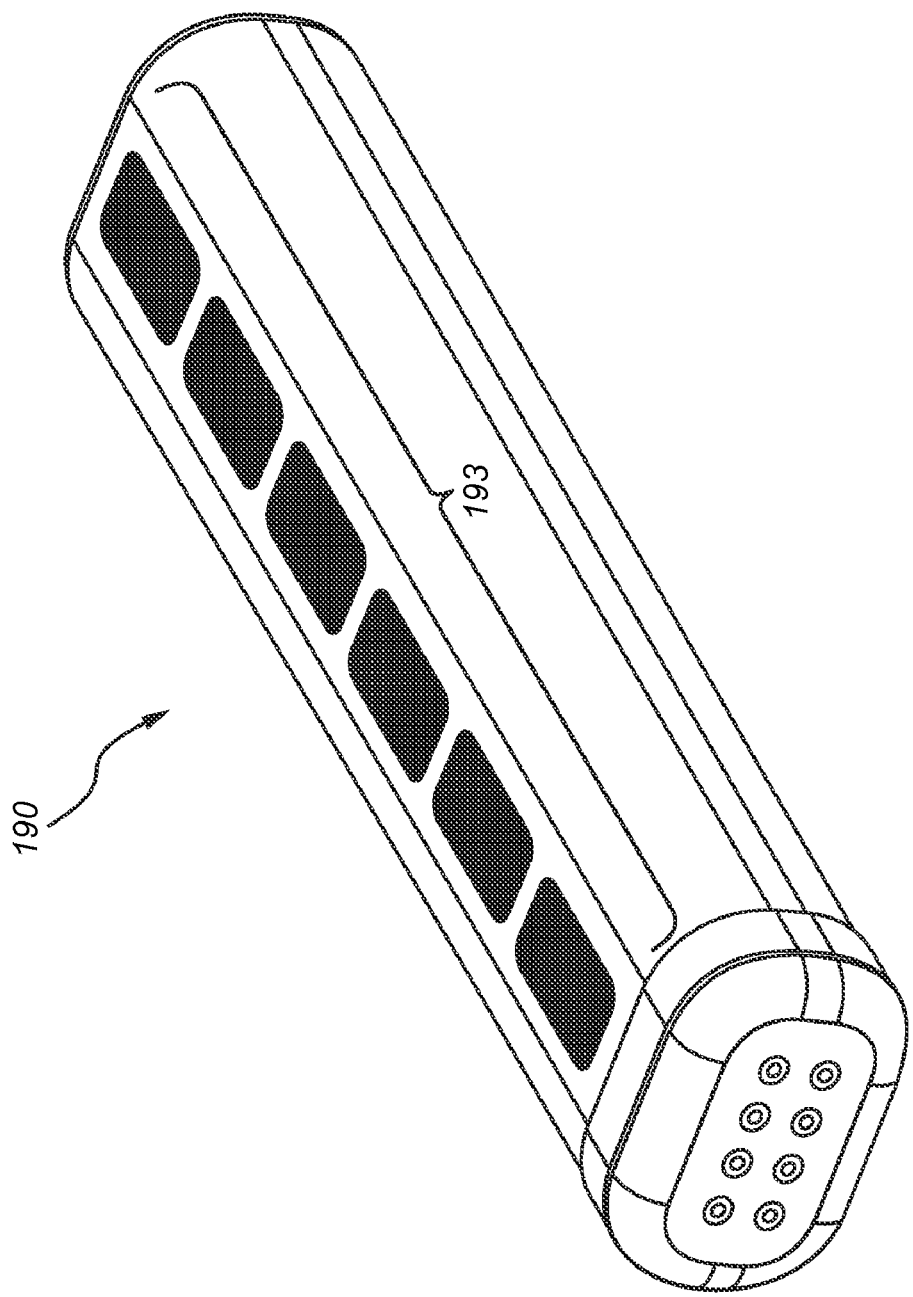
FIG. 10B shows an example of a microstimulator with a plurality of electrodes disposed on an outer surface thereof according to principles described herein.
Figure 10C:
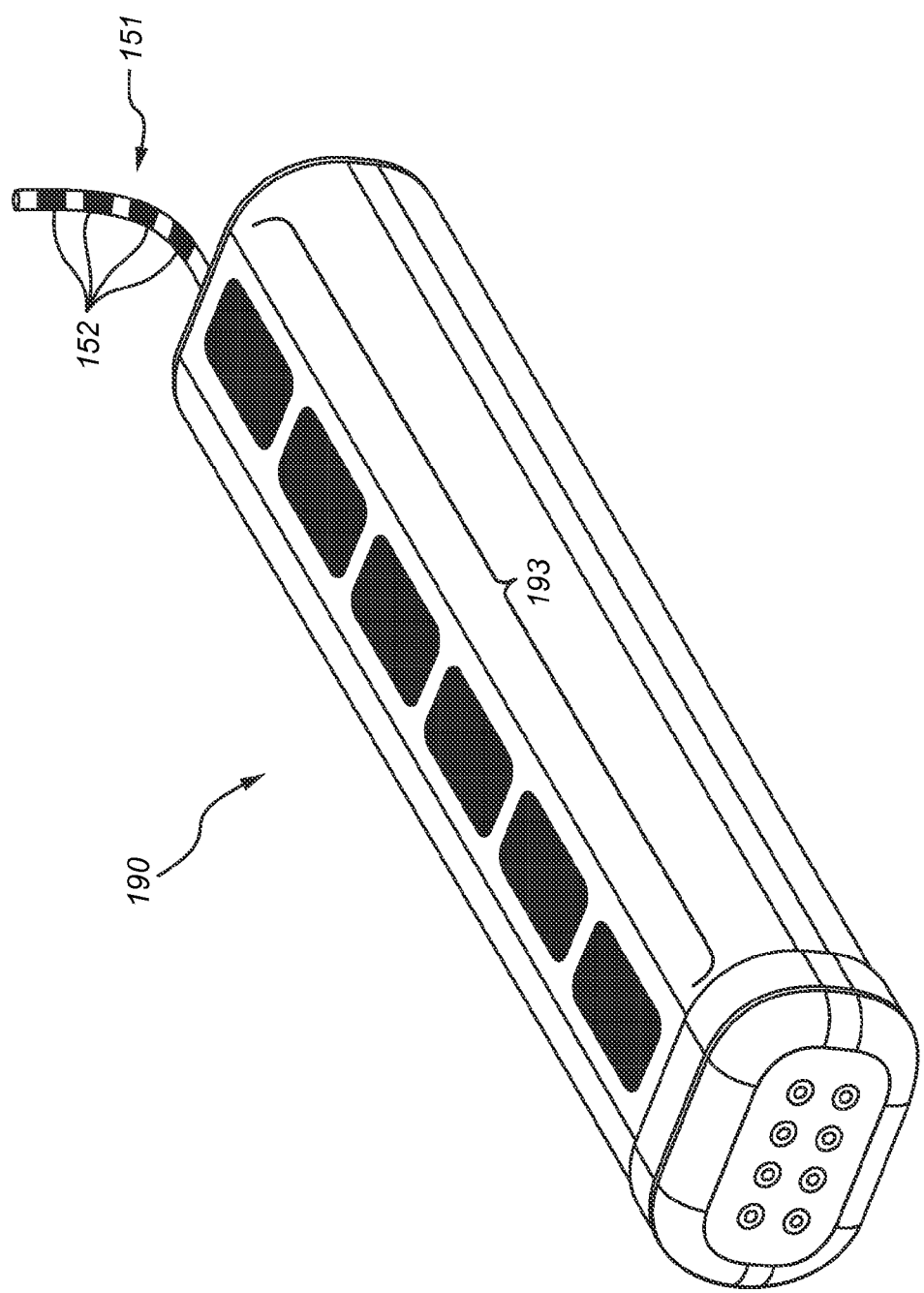
FIG. 10C shows the exemplary microstimulator of FIG. 10B coupled to a lead having a number of electrodes disposed thereon.

FIGS. 10A-10C show alternative configurations of a microstimulator 190. It will be recognized that the alternative configurations shown in FIGS. 10A-10C are merely illustrative of the many possible configurations of a microstimulator 190. For example, FIG. 10A shows an example of a microstimulator 190 with one or more leads 200 coupled thereto. As shown in FIG. 10A, each of the leads 200 may include one or more electrodes 201 disposed thereon. The microstimulator 190 of FIG. 10A may additionally or alternatively include one or more leadless electrodes 193 disposed on the outer surface thereof.

FIG. 10B illustrates an exemplary microstimulator 190 with a plurality of electrodes 193 disposed on an outer surface thereof. In some examples, any number of electrodes 193 may be disposed on the outer surface of the microstimulator 190. In some alternative examples, as shown in FIG. 100, the microstimulator 190 may be coupled to a lead 151 having a number of electrodes 152 disposed thereon. Each of the electrodes 193 and 152 may be selectively configured to serve as an anode or as a cathode.

Figure 11:
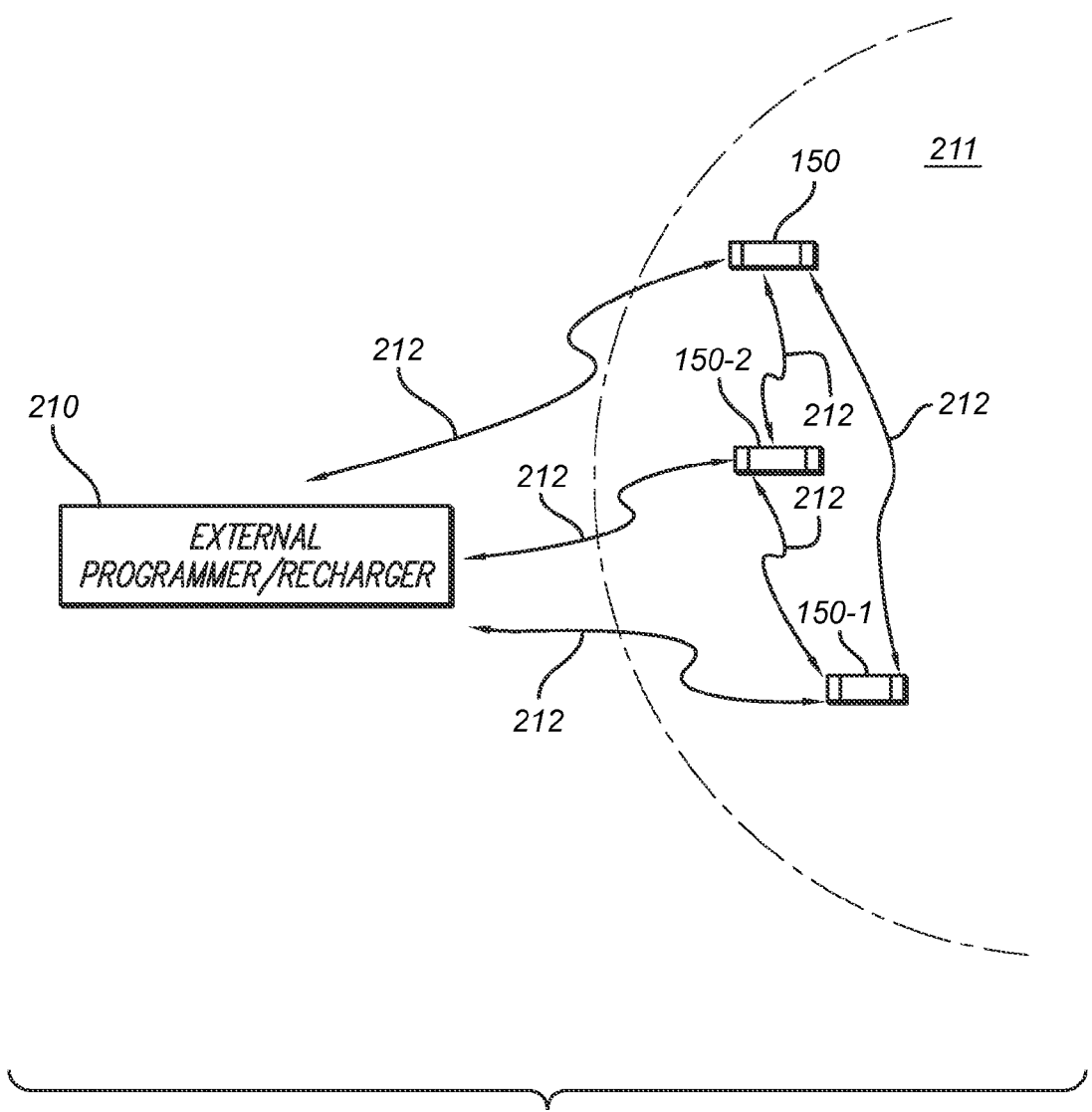
FIG. 11 depicts a number of stimulators configured to communicate with each other and/or with one or more external devices according to principles described herein.

In some examples, the stimulator 150 of FIG. 5 may be configured to operate independently. Alternatively, as shown in FIG. 11, the stimulator 150 may be configured to operate in a coordinated manner with one or more additional stimulators, other implanted devices, or other devices external to the patient's body. FIG. 11 illustrates an exemplary configuration wherein a first stimulator 150-1 implanted within the patient 211 provides a stimulus to a first location, a second stimulator 150-2 provides a stimulus to a second location, and a third stimulator 150-3 provides a stimulus to a third location. In some examples, one or more external devices 210 may be configured to control the operation of each of the implanted devices 210. In some embodiments, an implanted device, e.g., stimulator 150-1, may control, or operate under the control of, another implanted device(s), e.g., stimulator 150-2 and/or stimulator 150-3. Control lines 212 have been drawn in FIG. 11 to illustrate that the external device 210 may communicate or provide power to any of the implanted devices 150 and that each of the various implanted devices 150 may communicate with and, in some instances, control any of the other implanted devices.

As a further example of multiple stimulators 150 operating in a coordinated manner, the first and second stimulators 150-1 and 150-2 of FIG. 11 may be configured to sense various indicators of the symptoms or causes of damaged neural tissue and transmit the measured information to the third stimulator 150-3. The third stimulator 150-3 may then use the measured information to adjust its stimulation parameters and apply stimulation to the damaged neural tissue accordingly.

In order to determine the strength and/or duration of electrical stimulation required to effectively treat a particular damaged nerve, various indicators of the symptoms or causes of damaged neural tissue and/or a patient's response to treatment may be sensed or measured. To this end, the stimulator 150 may also include a sensor device configured to sense any of a number of indicators related to the damaged neural tissue. For example, the stimulator 150 may include and/or be in communication with a pressure sensor or any other device configured to sense pressure exerted on a nerve or within a canal or tunnel.

In some examples, the sensor device may be disposed on the lead 151. The sensor device may alternatively be included within a separate implanted or external device.

The indicators that may be sensed include, but are not limited to, pressure on a nerve or within a tunnel or canal, inflammation indicators, substance P levels, mechanical weakness, neurotransmitter levels, hormone levels, blood flow rate, medication levels within a patient, and patient input (e.g., when a patient feels pain associated with damaged neural tissue, the patient can push a button on a remote control or other external unit to initiate stimulation). In some examples, the stimulator 150 may be configured to adjust the stimulation parameters in a closed loop manner in response to one or more of these measurements.

Thus, one or more external devices may be provided to interact with the stimulator 150, and may be used to accomplish at least one or more of the following functions:

Function 1: If necessary, transmit electrical power to the stimulator 150 in order to power the stimulator 150 and/or recharge the power source 154.

Function 2: Transmit data to the stimulator 150 in order to change the stimulation parameters used by the stimulator 150.

Function 3: Receive data indicating the state of the stimulator 150 (e.g., battery level, drug level, stimulation parameters, etc.).

Additional functions may include adjusting the stimulation parameters based on information sensed by the stimulator 150 or by other sensing devices.

By way of example, an exemplary method of enhancing neural signal transmission within damaged neural tissue may be carried out according to the following sequence of procedures. The steps listed below may be modified, reordered, and/or added to as best serves a particular application.

1. A stimulator 150 is implanted so that its electrodes 152 are in communication with the damaged neural tissue. As used herein and in the appended claims, the term "in communication with" refers to the stimulator 150 and/or stimulating electrodes 152 being adjacent to, in the general vicinity of, in close proximity to, directly next to, or directly on the damaged neural tissue.

2. The stimulator 150 is programmed to apply a hyperpolarizing electrical stimulation current to the damaged neural tissue. The hyperpolarizing stimulation current may be in accordance with one or more stimulation parameters configured to enhance neural signal transmission within the damaged neural tissue.

3. When the patient desires to invoke stimulation, the patient sends a command to the stimulator 150 (e.g., via a remote control) such that the stimulator 150 delivers the prescribed stimulation to the damaged neural tissue. The stimulator 150 may be alternatively or additionally configured to continuously apply the stimulation to the damaged neural tissue and/or automatically apply the stimulation in response to sensed indicators of the symptoms and/or causes of the damaged neural tissue.

4. To cease stimulation, the patient may turn off the stimulator 150 (e.g., via a remote control).

5. Periodically, the power source 154 of the stimulator 150 is recharged, if necessary, in accordance with Function 1 described above.

In other examples, the electrical stimulation generated and applied by the stimulator 150 may be automatic and not controlled or invoked by the patient. It will be recognized that the particular stimulation methods and parameters may vary as best serves a particular application.

The stimulator 150 may be implanted within a patient using any suitable surgical procedure such as, but not limited to, small incision, open placement, laparoscopy, or endoscopy. Exemplary methods of implanting a microstimulator, for example, are described in U.S. Pat. Nos. 10,193,539; 5,193,540; 5,315,439; 6,185,452; 6,194,284; 6,208,894; and 6,051,020. Exemplary methods of implanting an SCS, for example, are described in U.S. Pat. Nos. 10,501,703; 6,487,446; and 6,519,227. All of these listed patents are incorporated herein by reference in their respective entireties.

Figure 12:
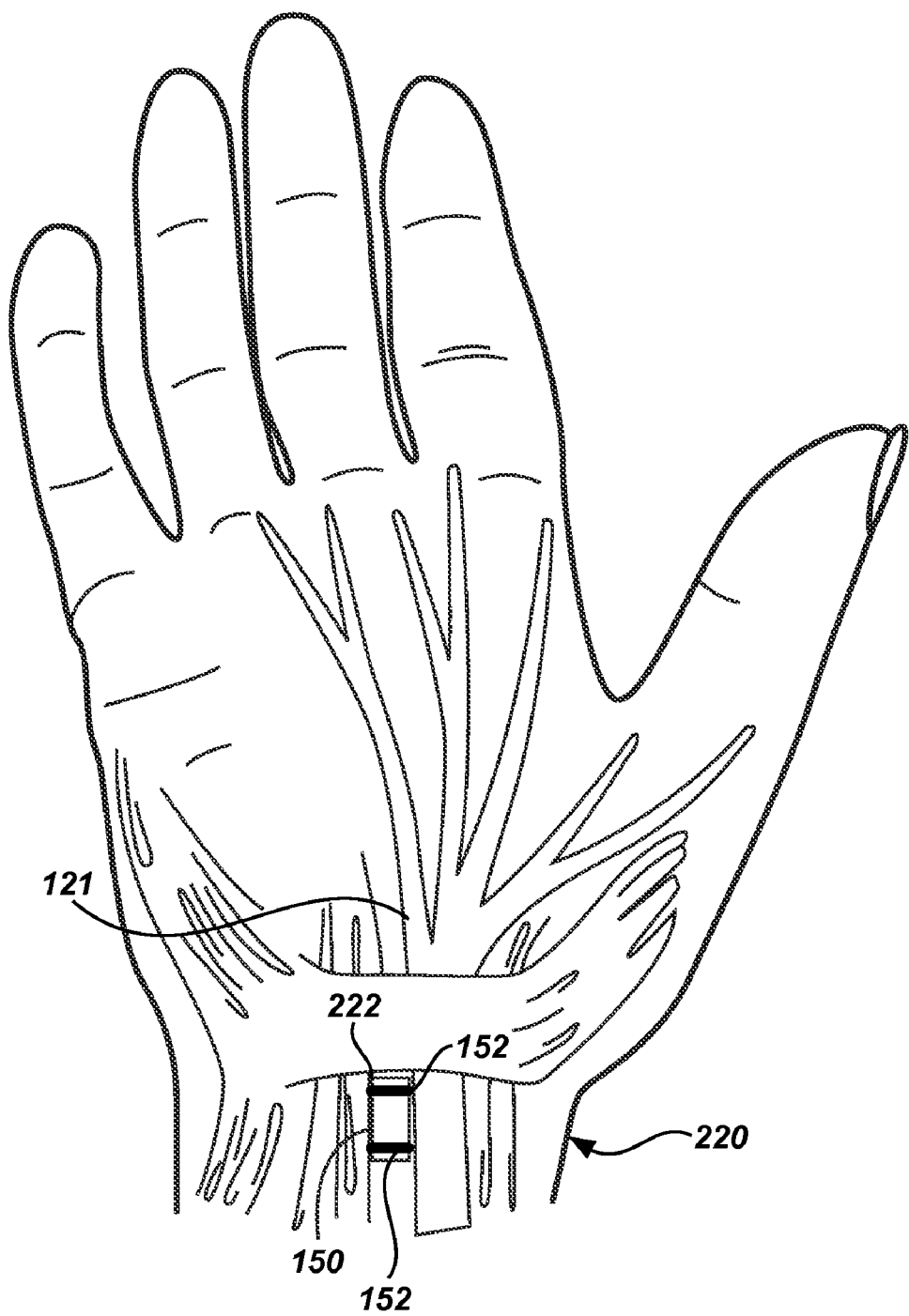
FIG. 12 shows a stimulator implanted within the wrist such that stimulation current may be applied to a portion of the median nerve that passes through the carpal tunnel according to principles described herein.

To illustrate, the stimulator 150 and/or electrodes 152 may be implanted such the electrodes 152 are in communication with a compressed nerve region. For example, FIG. 12 shows a stimulator 150 implanted within the wrist 220 such that stimulation current may be applied to a portion of the median nerve 221 that passes through the carpal tunnel 222. As shown in FIG. 12, the stimulator 150 is leadless and includes a number of electrodes 152 disposed on its surface. In this manner, stimulation may be applied to the median nerve 221 via the electrodes 152 in order to enhance neural signal transmission therethrough. It will be recognized that a lead with a number of electrodes 152 disposed thereon may additionally or alternatively be coupled to the stimulator and implanted such that the electrodes 152 are in communication with the carpal tunnel 222.

It will be recognized that the implant location of the stimulator 150 illustrated in FIG. 12 is merely illustrative and that the stimulator 150 and/or the electrodes 152 may additionally or alternatively be implanted at any other suitable location within the body.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
providing a stimulator;
programming said stimulator with one or more stimulation parameters configured to enhance transmission of a neural signal through damaged neural tissue; and
applying a hyperpolarizing electrical stimulation current with said stimulator to said damaged neural tissue in accordance with said one or more stimulation parameters;
wherein said hyperpolarizing electrical stimulation current is configured to enhance said transmission of said neural signal through said damaged neural tissue, wherein said hyperpolarizing electrical stimulation current comprises a stimulation pulse having a pulse width of less than 200 microseconds followed by a period of no stimulation.

2. The method of claim 1, wherein said hyperpolarizing electrical stimulation current is configured to open one or more h-gates of one or more voltage-gated sodium channels within said damaged neural tissue.

3. The method of claim 1, wherein said hyperpolarizing electrical stimulation current is configured to reduce an amplitude of a subsequent depolarizing signal required to trigger an action potential within said damaged neural tissue.

4. The method of claim 1, wherein said hyperpolarizing electrical stimulation current comprises a series of bursts of stimulation each followed by a period of no stimulation.

5. The method of claim 1, wherein said damaged neural tissue is a result of at least one or more of a nerve compression syndrome, a nerve ischemia, a radiation-induced injury, an inflammation, a degeneration, and a disease.

6. The method of claim 1, further comprising sensing at least one indicator of a symptom or cause of said damaged nerve tissue and using said at least one sensed indicator to adjust one or more of said stimulation parameters.

7. The method of claim 1, further comprising implanting said stimulator within a patient.

8. The method of claim 1, wherein said stimulator comprises at least one electrode disposed on an outer surface thereof, and wherein said method further comprises applying said hyperpolarizing electrical stimulation current via said at least one electrode.

9. The method of claim 1, wherein said stimulator is coupled to a lead having at least one electrode disposed thereon, and wherein said method further comprises applying said hyperpolarizing electrical stimulation current via said at least one electrode.

10. The method of claim 1, wherein applying the hyperpolarizing electrical stimulation current comprises periodically applying the stimulation pulse at a frequency of less than or equal to 10 kHz.

11. A method of enhancing transmission of a neural signal through damaged neural tissue, said method comprising:
implanting a stimulator within a patient;
programming said stimulator with one or more stimulation parameters configured to enhance transmission of said neural signal through said damaged neural tissue; and
modulating an operation of one or more voltage-gated sodium channels within said damaged neural tissue by applying a hyperpolarizing electrical stimulation current with said stimulator to said damaged neural tissue in accordance with said one or more stimulation parameters, wherein said hyperpolarizing electrical stimulation current comprises a stimulation pulse having a pulse width of less than 200 microseconds followed by a period of no stimulation.

12. The method of claim 11, further comprising opening one or more h-gates of said voltage-gated sodium channels with said hyperpolarizing electrical stimulation current.

13. The method of claim 11, wherein said hyperpolarizing electrical stimulation current is configured to reduce an amplitude of a subsequent depolarizing signal required to trigger an action potential within said damaged neural tissue.

14. The method of claim 11, wherein said hyperpolarizing electrical stimulation current comprises a series of bursts of stimulation each followed by a period of no stimulation.

15. The method of claim 11, further comprising sensing at least one indicator of a symptom or cause of said damaged nerve tissue and using said at least one sensed indicator to adjust one or more of said stimulation parameters.

16. A system for enhancing transmission of a neural signal through damaged neural tissue, said system comprising:
a stimulator configured to be implanted at least partially within a patient and to generate a hyperpolarizing electrical stimulation current in accordance with one or more stimulation parameters adjusted to enhance transmission of said neural signal through said damaged neural tissue;
a programmable memory unit in communication with said stimulator and programmed to store said one or more stimulation parameters to at least partially define said hyperpolarizing electrical stimulation current such that said hyperpolarizing electrical stimulation current is configured to enhance said transmission of said neural signal transmission through said damaged neural tissue; and
means, operably connected to said stimulator, for applying said hyperpolarizing electrical stimulation current to said damaged neural tissue, wherein said hyperpolarizing electrical stimulation current comprises a stimulation pulse having a pulse width of less than 200 microseconds followed by a period of no stimulation.

17. The system of claim 16, wherein said hyperpolarizing electrical stimulation current is configured to reduce an amplitude of a subsequent depolarizing signal required to trigger an action potential within said damaged neural tissue.

18. The system of claim 16, wherein said hyperpolarizing electrical stimulation current comprises a series of bursts of stimulation each followed by a period of no stimulation.

* * * * *